United States Patent [19]

Rosencwaig

[11] Patent Number: 4,484,820

[45] Date of Patent: Nov. 27, 1984

[54] METHOD FOR EVALUATING THE QUALITY OF THE BOND BETWEEN TWO MEMBERS UTILIZING THERMOACOUSTIC MICROSCOPY

[75] Inventor: Allan Rosencwaig, Danville, Calif.

[73] Assignee: Therma-Wave, Inc., Fremont, Calif.

[21] Appl. No.: 381,891

[22] Filed: May 25, 1982

[51] Int. Cl.³ .................... G01N 25/00; G01N 29/00; G01K 11/22

[52] U.S. Cl. .......................................... 374/6; 73/606; 73/643; 356/354; 374/117

[58] Field of Search .............. 374/117, 57, 6; 73/643, 73/606, 588, 582, 659, 643; 356/354

[56] References Cited

U.S. PATENT DOCUMENTS

| | | | |
|---|---|---|---|
| 3,008,029 | 11/1961 | Davis et al. | 374/57 X |
| 3,233,450 | 2/1966 | Fry | 73/620 |
| 3,842,663 | 10/1974 | Hartung et al. | 73/659 X |
| 4,011,748 | 3/1977 | Bond et al. | 73/618 X |
| 4,091,681 | 5/1978 | Hordvik | 73/574 |
| 4,137,991 | 2/1979 | Melcher et al. | 73/643 X |
| 4,218,922 | 8/1980 | Ensminger | 73/588 |
| 4,255,971 | 3/1981 | Rosencwaig | 73/606 |
| 4,267,732 | 5/1981 | Quate | 73/606 |
| 4,429,578 | 2/1984 | Darrel | 73/659 |

OTHER PUBLICATIONS

Publ.-G. S. Cargill, "Electronic Acoustic Microscopy", Physics Today, Oct. 1981, pp. 27–32.
Publ.-R. D. Weglein et al., "Scanning Acoustic Microscopy-Fault Detection", 15th Annual Reliability Physic Conference, pp. 37–43, 4/1977.
Publ.-S. K. Wang et al., "Nondestructive Visualization ... of Joints Using a Scanning Acoustic Microscope", pp. 171–175, IEEE 1977 Ultrasonics Symp.
Publ.-J. Attal et al., "Signal Processing in Reflective Acoustic Microscope", Electronics Letters, 7/20/78, vol. 14, No. 15, pp. 472–473.

*Primary Examiner*—Daniel M. Yasich
*Attorney, Agent, or Firm*—Limbach, Limbach & Sutton

[57] ABSTRACT

The subject invention relates to a method of evaluating the quality of the bond achieved between two members utilizing thermoacoustic microscopy. More particularly, thermoacoustic microscopy is used to detect and/or image the plate-mode resonant signature of bonded members to determine the quality of the bond therebetween. The method is particularly suited for analyzing the integrity of a bond between an integrated circuit die and a substrate. The subject method takes advantage of the fact that the plate-mode signature of a securely bonded die and substrate combination and a poorly bonded combination will be different. Accordingly, by detecting and/or imaging the plate-mode resonant signature of the sample the integrity of the bond can be assessed. Two techniques for carrying out the subject method are disclosed.

57 Claims, 2 Drawing Figures

METHOD FOR EVALUATING THE QUALITY OF THE BOND BETWEEN TWO MEMBERS UTILIZING THERMOACOUSTIC MICROSCOPY

The subject invention relates to a new and improved method for evaluating the quality of the bond achieved between two members utilizing thermoacoustics. More particularly, thermoacoustic microscopy is used to analyze the plate-mode resonant signature of bonded members to determine the quality of the bond therebetween.

BACKGROUND OF THE INVENTION

There is considerable interest in the non-destructive evaluation of the integrity of the mechanical bond between two structures. This interest has become particularly acute in the field of integrated circuit manufacturing. In the construction of an integrated circuit (IC) package, a small die, of silicon or other semiconductor material, is formed having the desired circuits printed thereon. The planar die is then bonded to a larger substrate such as a header, carrier or lead frame. The bond must have good mechanical strength and must provide a high level of thermal contact such that heat generated in the die during use is conducted to the substrate to prevent the die from overheating.

The necessity of creating a high quality bond is particularly important in the new, state of the art IC packages, where the dies are relatively large and generate more heat than ever before. Unfortunately, the bonding techniques now known do not always insure a high quality interconnection. The techniques used today frequently cause stresses to be generated in the silicon die which lead to an unsatisfactory bond. For example, one method of bonding includes the use of epoxy resins. When an epoxy resin cures, it shrinks or contracts causing stresses to build-up resulting in a poor quality bond. Another method employed is a solder technique carried out at a relatively higher temperature. However, as the components cool after the solder-bonding, differential contraction occurs also giving rise to stresses. Accordingly, since the bonding methods in use today are less than satisfactory, there is a great need for a means to evaluate integrity of the the bond achieved between the die and the substrate.

In the prior art, a few methods have been developed for evaluating the quality of the bond. For example, in die shear testing, the die is subjected to a mechanical force for examining the shear strength of the bond. This test, although direct, is generally destructive and thus not practical for automated large scale production. Other methods known in the prior art include x-ray radiography, infra-red microscopy, and transient thermal testing. Although the latter techniques are all essentially non-destructive, each has severe limitations related to applicability over a wide range of devices, reliability and possible automation.

Accordingly, it is an object of the subject invention to provide a new and improved method for non-destructively evaluating the quality of the bond between two members.

It is a further object of the subject invention to provide a new and improved method for assessing the integrity of the bond between two members which utilizes thermoacoustic microscopy.

It is another object of the subject invention to provide a new and improved method for evaluating the quality of the bond between two members by analyzing the plate-mode resonant signature of the combination.

It is still a further object of the subject invention to provide a new and improved method particularly suited for assessing the integrity of the bond achieved between an integrated circuit die and a substrate.

It is still another object of the subject invention to provide a new and improved method for obtaining the plate-mode resonant signatures of an integrated circuit die and substrate combination utilizing thermo-acoustic microscopy in order to evaluate the integrity of the bond achieved between the members.

SUMMARY OF THE INVENTION

In accordance with the above-stated objects, the subject invention provides a non-destructive method, utilizing thermoacoustic microscopy to assess the integrity of the bond between two structures. It is believed that thermoacoustic microscopy was first disclosed in applicant's prior U.S. Pat. No. 4,255,971, issued Mar. 17, 1981, which is incorporated herein by reference.

In thermoacoustic microscopy, a thermoacoustic signal is generated in a material by focusing a periodic localized heat source at a microscopic point. One way of generating the localized heating is by using an intensity modulated beam of electro-magnetic radiation. Typically, the radiation will be supplied by a laser, but can also be generated from an incoherent light source. Various wavelengths, such as x-rays, gamma rays, infrared, ultraviolet, visible light, microwaves or radio frequencies can be used. Thermoacoustic heating can also be generated through the thermal excitations arising from the interaction of the sample with a stream of particles such as a beam of electrons, protons, neutrons, ions, atoms or molecules. It is intended that the scope of subject invention include any of the above heating modes. The scope of the subject invention is also intended to include other heating methods, not yet perfected, as for example, spot heating by electrical resistance.

Irradiation of a sample with an intensity modulated beam of energy results in the periodic heating of the sample and in the generation of thermal waves. If the sample has a non-zero coefficient of thermal expansion, these thermal waves in turn give rise to elastic or acoustic waves of the same frequency. An acoustic detector, such as a piezoelectric transducer, in acoustic contact with the sample, will then record the intensity of the thermoacoustic waves. Other methods may be used for detecting the intensity of the acoustic waves including light detecting techniques such as laser interferometry and laser probes. (See "Probing of Acoustic Surface Perturbations by Coherent Light—R. L. Whitman and A. Korpel, Applied Optics, Vol. 8, No. 8, pp. 1567–1580, August 1969 and "Acoustic Surface Wave Amplitude and Phase Measurements Using Laser Probes", R. M. LaRue et al., Proc. IEE, Vol. 119, No. 2, pp. 117–125, February 1972). The recorded intensity is dependent upon many parameters, including the level of beam power absorbed by the sample, the modulation frequency, and various other thermal and elastic constants of the sample.

The intensity of thermoacoustic signals recorded by the detector will also depend on the various mechanical resonances of the sample. More particularly, when the heating is confined to a small region as compared to the acoustic wavelength, a major portion of the thermoacoustic energy is in the form of shear waves. These shear waves can excite plate-mode resonances in the sample. By varying the frequency of the modulation, various plate-mode resonances can be observed. As discussed more fully hereinbelow, plate-mode resonances in a sample can significantly affect the intensity of the acoustic signal received by the detector.

Plate-mode resonant signatures can be imaged using thermoacoustic microscopy. (See "Electron-Acoustic Microscopy"—G. S. Cargill, Physics Today, pp. 27-32, October 1981). Imaging is achieved by scanning the intensity modulated beam across the sample surface and recording the thermoacoustic signal as a function of beam position. At a modulation frequency corresponding to a plate-mode resonance of the sample, a pattern or signature of strong and weak areas will be recorded over the surface of the sample. This result is due to the fact that strong signals are generated when the beam is positioned at surface locations on the sample which coincide with the antinodes of the plate-mode pattern. Conversely, weak signals are generated when the beam is positioned at locations which coincide with the nodes of the plate-mode pattern.

The plate-mode resonance frequencies, the mode spacings in the pattern, and the intensity of the plate-mode vibrations, depend on a variety of factors including the elastic constants and the dimensions of the sample. Most importantly for this application, as the thickness of the sample increases, the resonance frequencies decrease, the mode spacings increase, and the intensity of the mode vibrations decrease.

The latter relationships concerning the sensitivity of the plate-mode resonance to the sample thickness, provides the basis for the method of the subject invention wherein thermoacoustic evaluation of bond integrity can be made between two members. More particularly, and in the case of an integrated circuit, a die that is poorly bonded to its substrate will exhibit a plate-mode signature defined primarily by the dimensions of the die itself. On the other hand, a die that is securely bonded to its support structure will exhibit a plate-mode signature indicative of the combined structure. Accordingly, by comparing the detected plate-mode signature of a sample with a predetermined signature such as one associated with either a poorly bonded combination or a securely bonded combination, the quality of the bond can be assessed.

In the particular example of an integrated circuit construction, a poorly bonded die will exhibit relatively intense plate-mode resonances. When the die is securely bonded to the substrate, a single more massive structure is defined. The resulting combination structure is typically many times thicker than the die alone. Accordingly, the plate-mode resonances will be sharply attenuated in the securely bonded situation thereby providing an excellent method of evaluating the integrity of the bond.

As discussed more fully hereinbelow, two techniques are disclosed for implementing the method of the subject invention. The first technique is particularly suited for the detailed evaluation of the bond between the sample members. In this technique, the modulation frequency of the periodic heating means is selected to produce a plate-mode resonant condition. The localized heating spot is then scanned in two dimensions over the surface of the sample. Conversely the heating spot is held stationary and the sample is rastered in two dimensions. The acoustic signals generated are detected and processed to produce an image of the plate-mode signature. This is then compared with a predetermined signature such as one associated with either a poorly bonded sample or a securely bonded sample. By comparing these signatures, the quality of the bond between the members of the sample can be determined. Additional information can be obtained by imaging the sample at other resonant frequencies and comparing plate-mode signatures.

The second technique, which is disclosed more fully hereinbelow, is particularly suited for evaluating the integrity of the bond in a production situation. In the second technique, the periodic heating means is focused at one location on the sample. The modulation frequency of the periodic energy is then varied. By this arrangement, the sample will be taken through various plate-mode resonances. The acoustic signals detected are then compared with a predetermined output associated with either a poorly bonded and a securely bonded combination. By this arrangement, the quality of the bond can be evaluated.

Further objects and advantages of the subject invention will become apparent from the following detailed description taken in conjunction with the drawings in which:

DESCRIPTION OF THE PREFERRED EMBODIMENTS

As discussed above, the subject method employs thermoacoustic imaging or detection of plate-mode resonances to evaluate the integrity of the bond between two elements. It is intended that the scope of the subject invention include a wide range of techniques for implementing the subject method. Two such techniques are discussed hereinbelow.

It is expected that the subject invention will be found particularly useful in the field of integrated circuit manufacture. Accordingly, the remainder of the disclosure will be related specifically to the construction of an integrated circuit package. However, it is to be understood that the scope of the subject invention is intended to apply to any situation where two structures are to be bonded together and will exhibit plate-like resonance characteristics.

Figure 1:
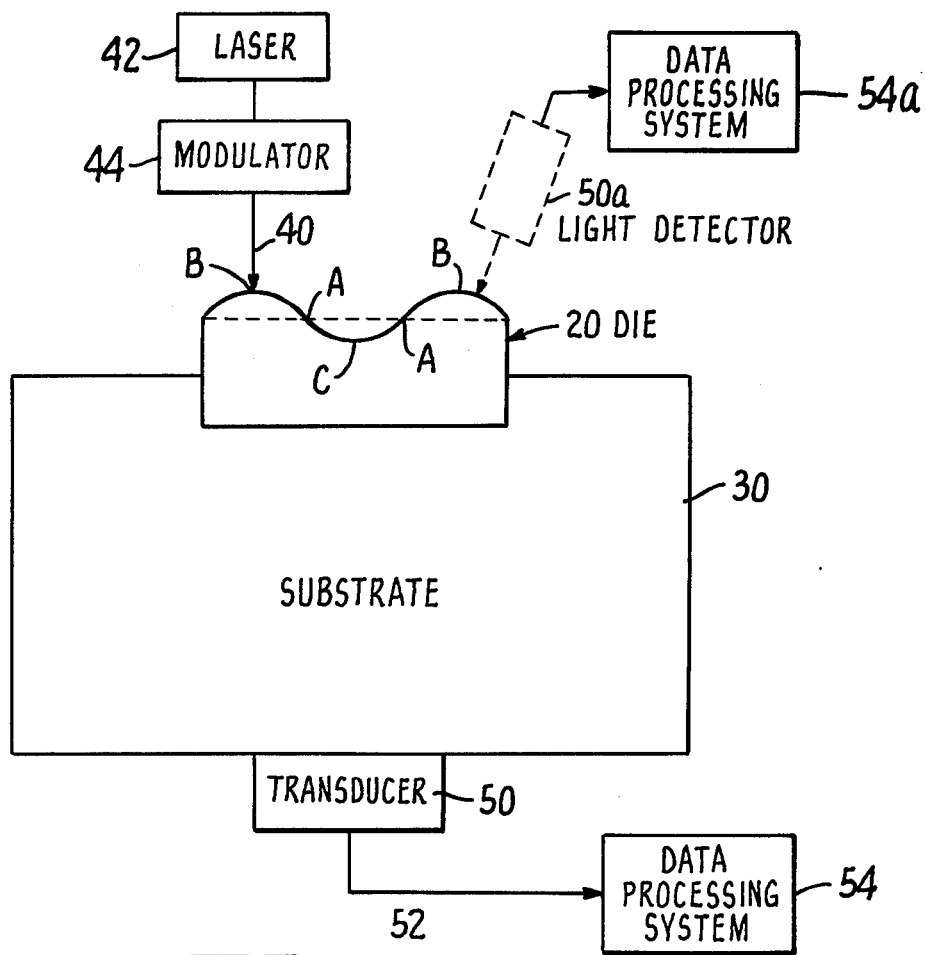
FIG. 1 is an illustration of an integrated circuit package exhibiting plate-mode resonance.

Referring to FIG. 1, in an integrated circuit construction, a relatively thin planar die 20, formed from a silicon or other semiconductor material, is bonded to a relatively massive substrate 30. In order to insure proper operation, this bond must be both mechanically and thermally satisfactory. In order to evaluate the mechanical bonding of the die to the substrate, the subject method utilizes thermoacoustic detection and/or imaging of the plate-mode patterns of the structure.

A thermoacoustic image is generated by focusing a periodic heat source 40 at a microscopic spot on the surface of the die 20. As discussed above, this periodic heating can be supplied by an intensity modulated energy beam defined by, for example, a laser 42 or a stream of particles such as an electron beam. In the case of an optical beam, periodic heating is achieved through the use of a modulator 16 such as an acoustic-optic or electro-optic modulator. When an intensity modulated beam 40 is focused on the surface of the die, periodic heating of the sample takes place which causes the generation of thermal waves. The thermal waves give rise to acoustic waves that can be detected for example, by a piezoelectric transducer 50. The signal 52 from the transducer 50 is then fed through suitable circuitry to a suitable data storage, processing and display system 54. Data processing system 54 is capable of performing the necessary comparisons of the signal output from the detector as described below. As pointed out above, various other detectors can be employed to sense the acoustic waves. For example, and as indicated in phantom line in FIG. 1, a light detector 50a defined by a laser probe or a laser interferometer, can be utilized. In the latter case, signals from light detector 50a are supplied to the data processing system 54a.

As illustrated in FIG. 1, at particular modulation frequencies of the energy beam, the upper surface of the die will exhibit plate-mode or standing wave patterns. As can be appreciated, the surface wave illustrated in FIG. 1 is greatly exaggerated for the purposes of clarity. The standing wave is defined by nodes and antinodes, the latter including both minima and maxima points. The nodes (labeled "A") are points on the standing wave which are at zero energy. The antinodes include maxima points B, having a high positive energy. One antinode minima C is illustrated which represents a point of high energy having an opposite phase as compared with the maxima B.

A free standing die 20 will generate a standing wave pattern having an intensity which, as discussed above, is dependant on many factors. As illustrated in FIG. 1, when the die 20 is bonded to the substrate 30, the combination presents a substantially thicker structure. With all other factors remaining the same, in a securely bonded construction, the intensity of plate-mode resonances will be significantly less than in the free standing situation. Accordingly, by investigating the plate-mode signature of the entire structure, evaluation of the quality of the bond can be made.

In the first technique of the preferred embodiment, a full thermal-wave or thermoacoustic image is produced. More particularly, after selecting a beam modulation frequency which will produce a plate-mode resonance, the beam 40 is scanned or rastered in a two-dimensional array over the surface of the die. Conversely, the beam can be held stationary and the sample rastered beneath it. The signals 52, sensed by the detector, are used to generate an image of the surface of the die.

The local acoustic condition on the surface of the die will substantially affect the intensity of the waves which are sensed by detector 50. More particularly, when the beam is located at a node A, only the energy in the beam itself is available to be transmitted to the detector 50. In contrast, significantly more energy is available when the beam is located at antinodes B and C. This result can be explained because the surface of the die is in resonance due to the periodic nature of the energy beam. Since the beam modulation and the plate-mode resonance are at the same frequency, the surface of the die acts as a pump to amplify the energy supplied by the beam. Accordingly, when the beam is located at an antinode, the intensity of the acoustic waves received at the detector will be substantially increased. As the beam is moved between nodes and antinodes, intermediate energy levels will be detected.

When the two dimensional scanning of the beam is completed, a two dimensional thermal-wave or thermoacoustic image of the surface of the die 20 can be generated. This image will include the image of the plate-mode resonance pattern for the sample at the beam modulation frequency selected. Various methods, including ultrasonic and optical techniques, can be used to generate the thermoacoustic image, some of which are discussed in the previously cited references and therefore need not be described.

In accordance with the subject method, if the die 20 is securely bonded to the substrate 30, the plate-mode image produced should correspond to a sample having the dimensions of the combination. In contrast, if the die is poorly bonded to the substrate, the image produced will tend to approach the image which would result if a free standing die was tested. Accordingly, by analyzing the image generated of the plate-mode signature, information can be obtained relating to the integrity of the bond. Additional analyses of the bond can be carried out by imaging the plate-mode signature of the structure at other resonant modulation frequencies. As can be appreciated, at different resonant frequencies, the location of the nodes and antinodes of the plate-mode pattern will be at different positions such that more information can be obtained. Plate-mode signatures obtained at different modulation frequencies would be compared to expected signatures at corresponding frequencies.

The second technique of the subject invention takes advantage of the fact that at different resonant frequencies the location of the nodes and antinodes vary. Accordingly, a significant amount of information can be generated by focusing the beam at a single point and varying the frequency of the modulation of the beam. This technique, as described more fully immediately below, is particularly suited for mass production situations where a rapid analysis of the integrity of the bond must be made. This technique can be readily applied to the manufacture of integrated circuit packages since the substrate 30 typically has a thickness much greater than the die 20 such that the difference in plate-mode signatures of a poorly bonded and a well bonded die is great. Accordingly, a reliable evaluation of bond integrity can be obtained without a detailed mode pattern analysis.

Figure 2:
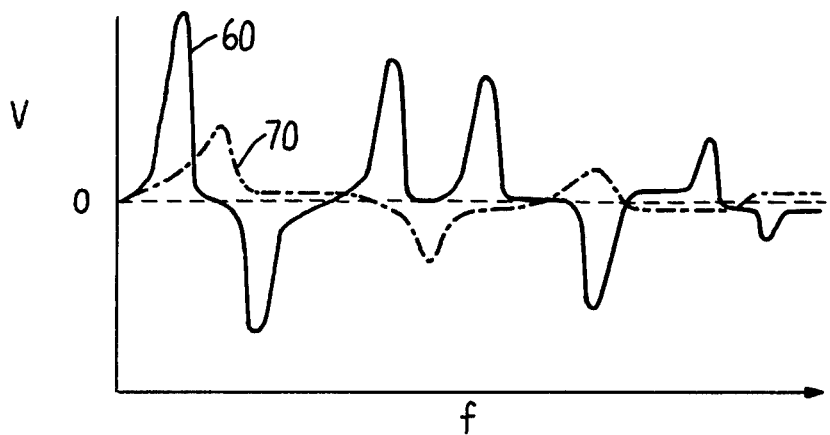
FIG. 2 is a graphic representation of a possible acoustic output detected in the second technique of the subject invention.

In the second technique of the subject invention, the intensity modulated beam of energy is focused at a single point. The frequency of the periodic beam is then varied and the acoustic signals detected are recorded as a function of the modulation frequency. Referring to FIG. 2, an example of the type of output signal which could be sensed by detector 50 is illustrated. FIG. 2 is a simplified representation for purposes of explanation. The Y-axis measures the voltage level sensed by detector 50, while the X-axis measures the change of the modulation frequency over time.

Curve 60 is intended to represent either a free standing die or a poorly bonded die construction. In this situation, a plurality of intense peaks and valleys are observed which correspond to instances where the beam 40 is coincident with antinodal points. As discussed above, when the beam is located on an antinodal point, the energy contained at the surface of the die acts as a pump for increasing the intensity of the acoustic waves.

Curve 70 is intended to represent the situation where the die 20 is securely bonded to the substrate 30. In the latter case, the resonant patterns are significantly damped such that there is little intensity modulation in the detected acoustic signals. By comparing the sensed signals from the detector with a predetermined value, such as for either the bonded or unbonded condition, an assessment can be made as to the quality of the bond between the die and the substrate.

A variety of methods could be used to analyze the signal sensed by detectors 50. One relatively simple method would be to rectify and integrate the signal over time. As can be appreciated, the integration of a rectified curve 60 will produce a value far greater than the integration of a rectified curve 70. Accordingly, given a particular set of parameters, fixed values could be assigned to various quality levels of bonding. By this arrangement, rapid sorting of IC packages into satisfactory and unsatisfactory classifications can be readily made.

In many cases, it may be possible to define a frequency above which a well-bonded die will produce no discernable plate-mode signals, while a poorly bonded die will produce such signals. In such cases, the signal analysis will be greatly facilitated.

The accuracy of the assessment of the bond integrity could, of course, be further enhanced by taking successive readings at more than one point on the sample. For example, after the first signals are detected, the beam position can be shifted to a second location to obtain new readings for confirming or enhancing the analysis.

In summary, there has been provided a new and improved method for evaluating the quality of the bond between a first and second member combination. The method analyzes the plate-mode characteristics of the members using thermoacoustic detection and/or imaging. The method takes advantage of the fact that the plate-mode signature of a securely bonded combination and a poorly bonded combination will be different. Accordingly, in the subject method, the sample is subjected to periodic localized heating to produce thermal waves which in turn produce acoustic waves of a longer wavelength. The acoustic waves are detected and processed to obtain the plate-mode signature of the combination. The signature which is obtained is compared a predetermined plate-mode signature such as one associated with either a poorly bonded or a securely bonded combination whereby the integrity of the bond can be assessed.

While the subject invention has been described with reference to preferred embodiments, it is to be understood that various other changes and modifications could be made therein, by one skilled in the art, without varying from the scope and spirit of the subject invention as defined by the appended claims.

I claim:

1. A method for evaluating the quality of the bond achieved between a combination of a first and second member comprising the steps of:
    causing a periodic localized heating in at least one microscopic spot in said first member to produce thermal waves which in turn give rise to acoustic waves of a longer wavelength that propagate through said combination with the frequency of said periodic heating causing said combination to resonate;
    detecting the acoustic waves produced in said combination and generating signals therefrom;
    processing said signals to obtain a plate-mode resonant signature of said first and second member combination; and
    comparing said obtained plate-mode resonant signature to a predetermined plate-mode resonant signature associated with a similar combination where the quality of the bond is known whereby the quality of the bond between said members can be evaluated.

2. The method as recited in claim 1 further including the step of scanning the first member, with said localized heated spot, in a two dimensional array of microscopic spots and processing said signals as a function of the position of said localized heating to generate a two dimensional image of the plate-mode resonant signature of said combination.

3. The method as recited in claim 1 further including the step of varying the frequency of said periodic localized heating while maintaining said heating at a single spot in order to generate a plurality of plate-mode resonances.

4. The method as recited in claim 1 wherein the source of said localized heating is an intensity modulated beam of energy.

5. The method as recited in claim 4 wherein said beam of energy is defined by electromagnetic radiation.

6. The method as recited in claim 5 wherein said electromagnetic radiation is defined by light.

7. The method as recited in claim 6 wherein said light is generated from a laser and is coherent.

8. The method as recited in claim 4 wherein said beam of energy is defined by a stream of particles.

9. The method as recited in claim 8 wherein the particles in said beam are electrons.

10. The method as recited in claim 1 wherein said source of localized heating is defined by an electrical resistance.

11. The method as recited in claim 1 wherein said detector is an ultrasonic transducer.

12. The method as recited in claim 11 wherein said ultrasonic transducer is a piezoelectric detector.

13. The method as recited in claim 1 wherein said detector is a laser probe.

14. The method as recited in claim 1 wherein said detector is a laser interferometer.

15. A method for evaluating the quality of the bond achieved between a combination of a first and second member comprising the steps of:
    causing a periodic localized heating at a microscopic spot in said first member to produce thermal waves which in turn give rise to acoustic waves of a longer wavelength that propagate through said combination and with the frequency of said periodic heating being selected to cause said combination to resonate and exhibit a plate-mode signature;
    detecting the acoustic waves produced in said combination and generating signals therefrom;
    scanning said first member with said localized heating in a two-dimensional array of microscopic spots;
    processing said detected signals as a function of the position of said heated spot to generate a two-dimensional image of the plate-mode resonant signature of said combination; and
    comparing said generated image of said plate-mode resonant signature to a predetermined plate-mode resonant signature associated with a similar combination where the quality of the bond is known whereby the quality of the bond between said members can be evaluated.

16. The method as recited in claim 15 wherein the source of such localized heating is an intensity modulated beam of energy.

17. The method as recited in claim 16 wherein said beam of energy is defined by electromagnetic radiation.

18. The method as recited in claim 17 wherein said electromagnetic radiation is defined by light.

19. The method as recited in claim 18 wherein said light is generated from a laser and is coherent.

20. The method as recited in claim 16 wherein said beam of energy is defined by a stream of particles.

21. The method as recited in claim 20 wherein the particles in said beam are electrons.

22. The method as recited in claim 15 wherein said source of localized heating is defined by an electrical resistance.

23. The method as recited in claim 15 wherein said detector is an ultrasonic transducer.

24. The method as recited in claim 23 wherein said ultrasonic transducer is a piezoelectric detector.

25. The method as recited in claim 15 wherein said detector is a laser probe.

26. The method as recited in claim 15 wherein said detector is a laser interferometer.

27. A method for evaluating the quality of the bond achieved between a combination of a first and second member comprising the steps of:

causing a periodic localized heating at a microscopic spot in said first member to produce thermal waves which in turn give rise to acoustic waves of a longer wavelength that propagate through said combination;

detecting the acoustic waves produced in the combination and generating signals therefrom;

varying the frequency of the periodic heating while maintaining said heating at a single point to generate a plurality of plate-mode resonances in said combination; and comparing the detected signals to a set of predetermined signals associated with a similar combination where the quality of the bond is known whereby the quality of the bond between said members can be evaluated.

28. The method as recited in claim 27 wherein the source of said localized heating is an intensity modulated beam of energy.

29. The method as recited in claim 28 wherein said beam of energy is defined by electromagnetic radiation.

30. The method as recited in claim 29 wherein said electromagnetic radiation is defined by light.

31. The method as recited in claim 30 wherein said light is generated from a laser and is coherent.

32. The method as recited in claim 28 wherein said beam of energy is defined by a stream of particles.

33. The method as recited in claim 32 wherein the particles in said beam are electrons.

34. The method as recited in claim 27 wherein said source of heating is defined by an electrical resistance.

35. The method as recited in claim 27 wherein said detector is an ultrasonic transducer.

36. The method as recited in claim 35 wherein said ultrasonic transducer is a piezoelectric detector.

37. The method as recited in claim 27 wherein said detector is a laser probe.

38. The method as recited in claim 27 wherein said detector is a laser interferometer.

39. A method for evaluating the quality of the bond achieved between a combination of an integrated circuit die and a substrate comprising the steps of:

causing a periodic localized heating at a microscopic spot in said die to produce thermal waves which in turn give rise to acoustic waves of a longer wavelength that propagate through said combination;

detecting the acoustic waves produced in said combination and generating signals therefrom;

varying the frequency of said periodic heating while maintaining said heating at a single spot to generate a plurality of plate-mode resonances in said combination; and comparing the detected signals to a set of predetermined signals associated with a similar combination where the quality of the bond is known whereby the quality of the bond between said die and substrate can be evaluated.

40. The method as recited in claim 39 wherein the source of said localized heating is an intensity modulated beam of energy.

41. The method as recited in claim 40 wherein said beam of energy is defined by electromagnetic radiation.

42. The method as recited in claim 41 wherein said electromagnetic radiation is defined by light.

43. The method as recited in claim 42 wherein said light is generated from a laser and is coherent.

44. The method as recited in claim 40 wherein said beam of energy is defined by a stream of particles.

45. The method as recited in claim 44 wherein the particles in said beam are electrons.

46. The method as recited in claim 39 wherein said source of heating is defined by an electrical resistance.

47. The method as recited in claim 39 wherein said detector is an ultrasonic transducer.

48. The method as recited in claim 47 wherein said ultrasonic transducer is a piezoelectric detector.

49. The method as recited in claim 39 wherein said detector is a laser probe.

50. The method as recited in claim 39 wherein said detector is a laser interferometer.

51. An apparatus for evaluating the quality of the bond achieved between a combination of a first and second member comprising:

means generating a periodic localized heating in at least one microscopic spot in said first member to produce thermal waves which in turn gives rise to acoustic waves of longer wavelength which propagate through said combination in a manner to cause said combination to resonate;

means for detecting the acoustic waves generated in said combination;

means for processing the detected acoustic waves to obtain a plate-mode resonant signature; and means for comparing the obtained plate-mode resonant signature to a predetermined plate-mode resonant signature associated with a similar combination where the quality of the bond is known, whereby the quality of the bond between the members can be evaluated.

52. An apparatus as recited in claim 51 wherein said heating means further includes a means for varying the frequency of the periodic heating.

53. An apparatus as recited in claim 52 wherein said means for varying the frequency is a modulator.

54. An apparatus as recited in claim 51 wherein said means for generating localized heating is defined by an intensity modulated beam of energy.

55. An apparatus as recited in claim 51 further comprising:

means for scanning the first member with said localized heated spot in a two-dimensional array of microscopic spots; and means for processing said signals as a function of the position of said localized heating to generate a two-dimensional image of the plate-mode resonant signature of said combination.

56. An apparatus as recited in claim 51 wherein said means for detecting acoustic waves generated in said combination is defined by a piezoelectric transducer.

57. An apparatus as recited in claim 51 wherein said means for detecting the acoustic waves generated in said combination is defined by a laser probe.

* * * * *